United States Patent [19]
Berci

[11] Patent Number: 4,987,488
[45] Date of Patent: Jan. 22, 1991

[54] VIDEO SYSTEM FOR VISUALIZING MICROSURGICAL IMAGES WITH ENHANCED DEPTH OF FIELD

[76] Inventor: George Berci, 1271 Stoner Ave. #409, Los Angeles, Calif. 90025

[21] Appl. No.: 164,517

[22] Filed: Mar. 7, 1988

[51] Int. Cl.$^5$ ............................................. H04N 7/18
[52] U.S. Cl. .................................... 358/93; 358/225; 358/100
[58] Field of Search .................. 358/98, 93, 100, 107, 358/225; 350/508, 509, 519

[56] References Cited

U.S. PATENT DOCUMENTS

| | | | |
|---|---|---|---|
| 3,919,475 | 11/1975 | Dukich et al. | 358/225 X |
| 4,138,191 | 2/1979 | Peyman et al. | 350/502 |
| 4,598,311 | 7/1986 | Bellina | 358/93 |
| 4,672,559 | 6/1987 | Jansson et al. | 358/93 X |
| 4,769,698 | 9/1988 | Ledley et al. | 358/93 |

Primary Examiner—Victor R. Kostak
Attorney, Agent, or Firm—Marvin H. Kleinberg

[57] ABSTRACT

A high resolution video camera is equipped with a multi focal lens. The optical system is adjusted to provide a depth of field so that objects remain in focus. A high resolution, large screen color video monitor provides a greatly magnified view of the surgical field, permitting a surgeon to perform procedures directly from the screen image. Low light levels can be permitted and multiple monitors can be employed. Images can be stored on a disc or VCR and individual frames can be printed for a permanent record.

22 Claims, 3 Drawing Sheets

VIDEO SYSTEM FOR VISUALIZING MICROSURGICAL IMAGES WITH ENHANCED DEPTH OF FIELD

BACKGROUND OF THE INVENTION

The present invention relates to electro optical systems and, more particularly, to an improved system and method for visualizing objects within a surgical field in aid of microsurgical procedures.

Physicians and especially surgeons have long had the need to see, in detail, minute anatomical structures upon which they wish to operate during the course of a procedure. In many instances, the operating field is sufficiently exposed and accessible so that the naked eye is adequate for the work at hand. When, however, the objects in the field are too small to be easily seen with the naked eye, some form of magnification and micro instrumentation is necessary to permit a visualization of the working area.

Typical examples of procedures which require magnification in order to properly visualize the areas of interest are ear surgery (e.g stapedius mobilization), laryngeal surgery (the removal of tumors), neurosurgery (removal of aneurysms), gynecological surgery (repair divided tubes), urological surgery (anastomosis of a divided vas), hand surgery to suture small tendons, trauma surgery for the reimplantation of amputated extremities, and ophthamological procedures, just to name a few.

For many years, optical instrument makers provided microscopes, both monocular and binocular, which permitted a surgeon to view the surgical field with a selected magnification. Such instruments tend to be large, bulky, and require either a wall or ceiling mounting or a large stand to support the optics without undue vibration. These surgical microscopes were provided with a lens system that permitted some distance between the field (object) and the eyepieces. This distance is necessary so that the surgeon can introduce instruments between the microscope and the object under visual control.

Moreover, such systems required careful alignment and focussing, especially if the depth of field is limited to a plane of approximately one to two millimeter thickness. In addition, an illumination system was required which either projected a spotlight on the field through the optical system or used an external source with a fiber cable that could be attached to the microscope head.

With the advent of surgical microscopes, many so-called microsurgical procedures were attempted successfully, permitting the repair, restoration or implantation of many small organs. Nevertheless, disadvantages include, among other things, the size and weight of the instrument which requires time consuming efforts to adjust and direct it, and the need to accommodate an assistant, which generally requires a second station and a beam splitter with the attendant diminution of the light at the primary eyepiece.

The use of the conventional binocular microscope imposes its own special problems upon the surgeon who must remain more or less immobilized in order to view the field through the binocular eyepieces. Viewing through the small pupil of an eyepiece also causes fatigue in the viewer, especially if the procedure is a long and difficult one.

In many of these microscopes, when beamsplitters are used to provide a second viewing station, to be utilized by an assistant, or for documentation purposes by mounting cameras or the like, the available illumination must be divided among all of the stations. In a purely optical system, each time a beamsplitter is employed, the brightness of the transmitted image is reduced, thereby limiting the number of viewing stations by the extent to which the field can be illuminated. If the light intensity must be increased to provide adequate illumination at each viewing station, then the problem of increased heat must be dealt with and the operating field should not be overheated.

If cameras are utilized for still or motion picture photography, or, as in more modern systems, video cameras are employed which are coupled to videotape machines or video monitors, lower levels of light can be accepted by going to faster films or more sensitive electronic systems. It is, of course, possible to use electronic light amplification techniques with the video system, enabling a record to be made under marginal viewing conditions.

Once the patient is readied, the microscope must be trained on the field of interest and focussed. If any photographs are taken, they will appear substantially "flat" and planar since only a fairly "thin" section is in focus at any given time and if a feature or artifact that is closer or farther from the focal plane is to be viewed, the focus of the microscope must be readjusted. Since the optimum image in a surgeon's eyepiece may not result in the sharpest image for the camera, the focussing procedure may become quite time consuming.

Video cameras have taken a greater role in the surgical operating room with the advent of lighter, smaller and higher resolution sensor systems. To some extent, the mere transmission of an image from the photosensitive transducer area of the video camera to the much larger screen of the monitor provides some degree of magnification with acceptable image resolution.

BRIEF SUMMARY OF THE INVENTION

The present invention is intended to alleviate many of the shortcomings of the conventional surgical microscope and to provide many benefits that are presently unavailable. The key to the present invention is the use of a high resolution, miniaturized color video camera with a sensor area of approximately 6–7 mm diameter. An optical system brings the image of an object whose diameter is approximately 20 mm to the sensor element.

An optical system is selected to have a working distance of from 200 to 500 mm from the camera to the object plane with a depth of field in excess of 15 mm. This working distance permits the introduction of surgical instruments directly into the surgical field without interference with the optical system. In order to accomplish this, the optical system can employ a vari-focal or "zoom" lens whose focus can be varied from 150 mm to 400 mm. With such an optical system, most, if not all, of the operating field can remain in focus without adjusting the system.

The use of an all electronic system enables the use of a large screen, high resolution monitor to present the working area to the surgeon as well as to assistants, magnified to adequated detail according to need. Because the system is electronic, additional monitors can be placed in different locations for use by others in the surgical team or by students and spectators.

The electronic video signal can also drive video recorders, video storage discs, still cameras and/or printers which are capable of giving a "hard copy" record of any particular scene that is shown on the monitor to provide a permanent record of the procedure. A video tape can permit a careful review of the procedure, in "slow" motion or with "freeze frames" if desirable.

Further advantages and features of the present invention will be more fully apparent to those skilled in the art to which the invention pertains from the ensuing detailed description thereof, regarded in conjunction with the accompanying drawings wherein like reference numerals refer to like parts throughout and in which:

BRIEF DESCRIPTION OFT HE DRAWINGS

DETAILED DESCRIPTION OF THE DRAWINGS

Figure 1:
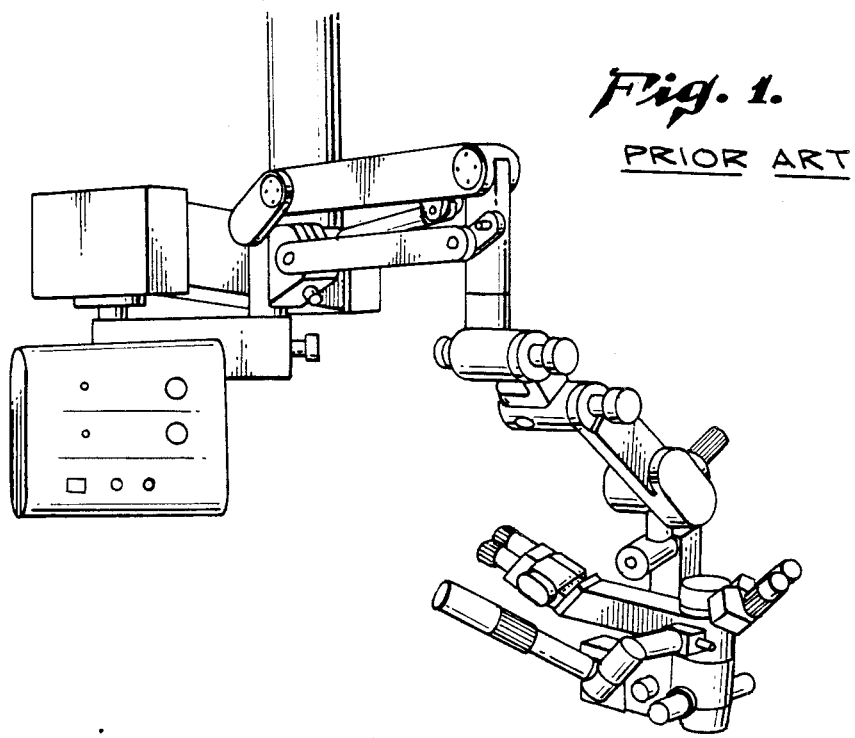
FIG. 1 is a side view of a prior art optical microscope.

Turning first to FIG. 1, there is shown a conventional, prior art surgical microscope of the type commercially available from Wild Heerbrugg Ltd. of Heerbrugg, Switzerland. Illustrated is an arrangement which employs two binocular eyepieces and a monocular tube all of which receive the same image through an internal beam splitter (not shown). Such an arrangement can be suspended from a built in overhead support frame, which can also support ancillary illuminating sources and electronic controls for remotely operated focus adjustments. Alternatively, a floor stand can also support the microscope in all of its complexity.

Apart from the size and weight, the need to view all of the surgical activities through the eyepieces of the binocular tubes, which remain in a fixed position throughout the procedure, can create fatigue and eyestrain and makes an otherwise difficult task even more so.

Figure 2:
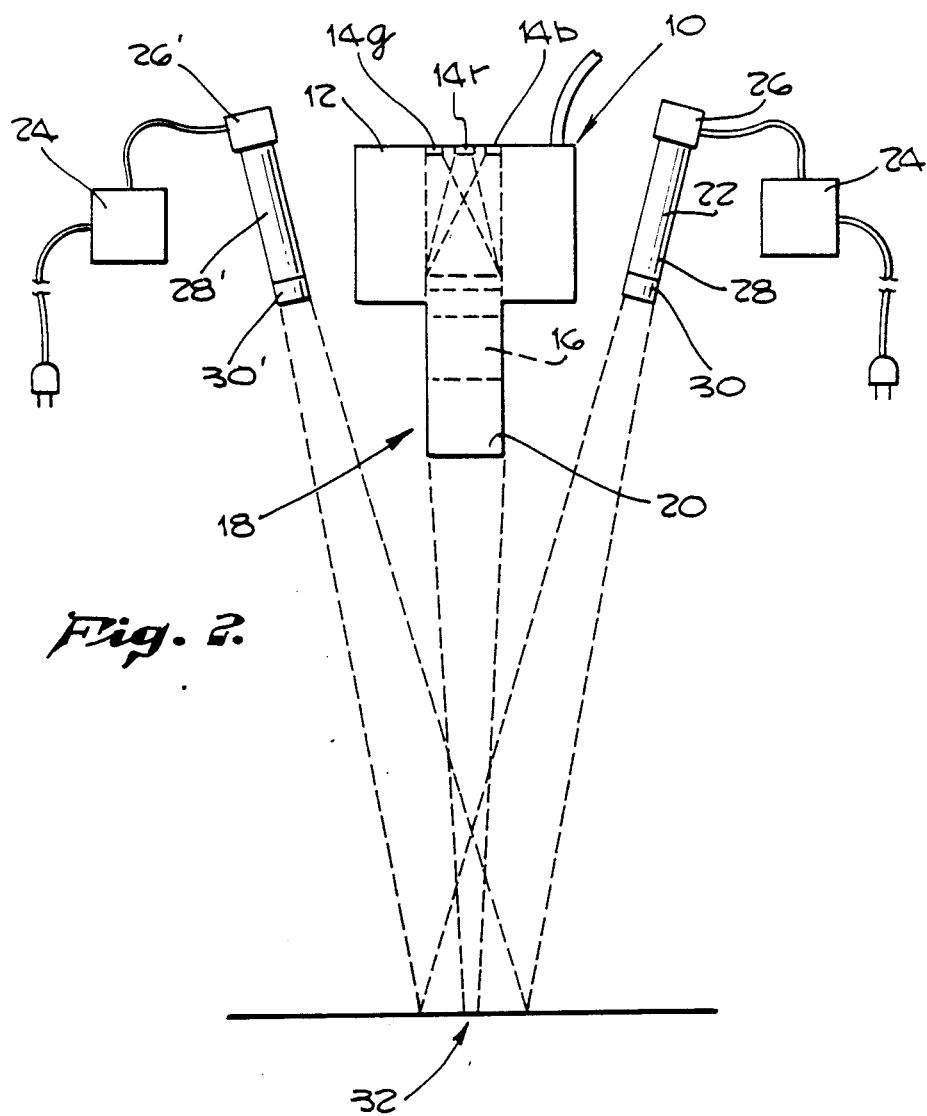
FIG. 2 is a side view of an electronic microscope according to the present invention.

Turning next to FIG. 2, there is shown an electronic video system 10, according to the present invention. The video system 10 includes a high resolution, color, miniature video camera 12, preferably employing 3 charge coupled diode ("CCD") sensors 14r, 14g, 14b, one for each of the principal colors (red, green and blue). An appropriate color separating device 16 is provided to supply an appropriate image to each of the sensors.

In a preferred embodiment, a high resolution camera is employed capable of resolving 510 horizontal by 492 vertical picture elements or "pixels". The sensing area for each color is approximately 6.6×8.8 mm. Preferably, the system is operated as an NTSC color system with a horizontal resolution of 520 lines.

An optical system 18 preferably utilizes a "zoom" or varifocal lens 20 which can be adjusted from 150 to 400 mm object distances. The aperture of the lens is stopped down sufficiently to provide a depth of field greater than 15 mm at the working distances. Because an electronic sensor system is employed, levels of light can be employed which are substantially lower than those that are required in the prior art optical microscopes.

Mounted adjacent the optical system 18 is a light projecting system 22 which can include a power supply 24, a light source 26, a fluid light transmission cable 28 and a condenser lens 30 which directs the light to an operating field 32. In alternative embodiments, if greater illumination is required, a second power supply 24', light source 26', fluid (light) cable 28' and condenser lens 30' can be added to bring additional brightness to the field 32.

Figure 3:
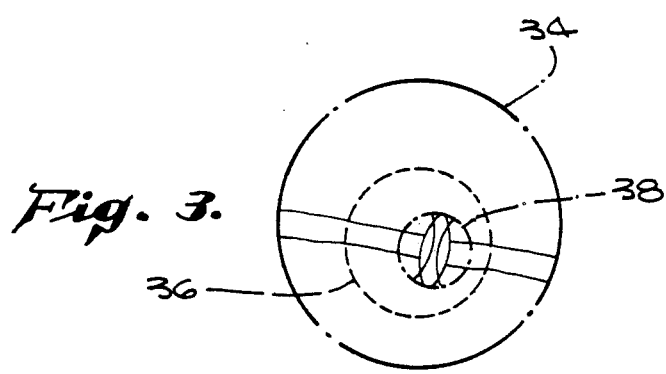
FIG. 3 is a top view of an operating field, showing the area of interest.

Turning next to FIG. 3, the operating field of interest 32 is illustrated. As shown, a first dashed circle 34 indicates the area under illumination. A dotted circle 36 circumscribes the field of view of the lens 20. A dash-dot circle 38 indicates the particular portion of the field of view that will be enlarged and displayed on a video monitor for use by the surgeon.

As seen, the actual area of interest to the surgeon is substantially smaller than the area that is illuminated and somewhat smaller than the area that can be "seen" by the lens 20.

Figure 4:
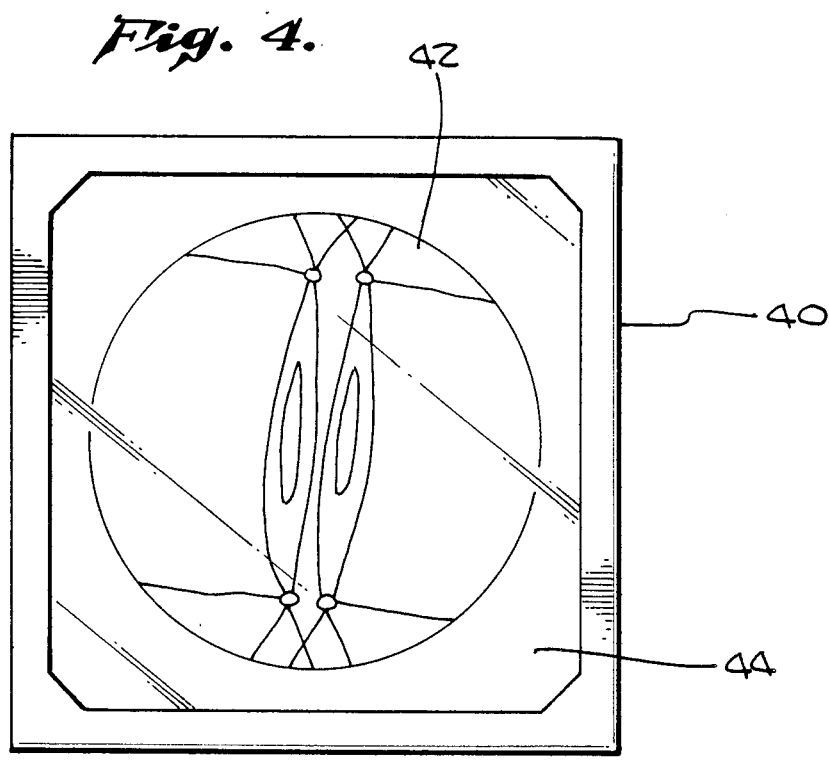
FIG. 4 is a view of a video monitor displaying the area of interest.

In FIG. 4, a high resolution, video color monitor 40 displays an enlarged image 42 of the object. This is due in part to the relative sizes of the sensing areas 14r, 14b, 14g (6.6mm×8.8mm) and the video monitor screen 44 (19" diagonal or larger) as well as the magnification of the image through the use of the lens (3× to 5×). This image 42 is large enough and bright enough to enable a surgeon to work from the screen 44 rather than through the binocular eyepieces of a conventional surgical microscope.

Because it is a simple thing to provide more than one monitor and because the size of the screen 44 is limited only by the type of monitor selected (since direct viewing displays are available in sizes up to 40" diagonally), assistants and observers can all view the object of interest and assistants can use the same or a different monitor to participate in the procedure.

Figure 5:
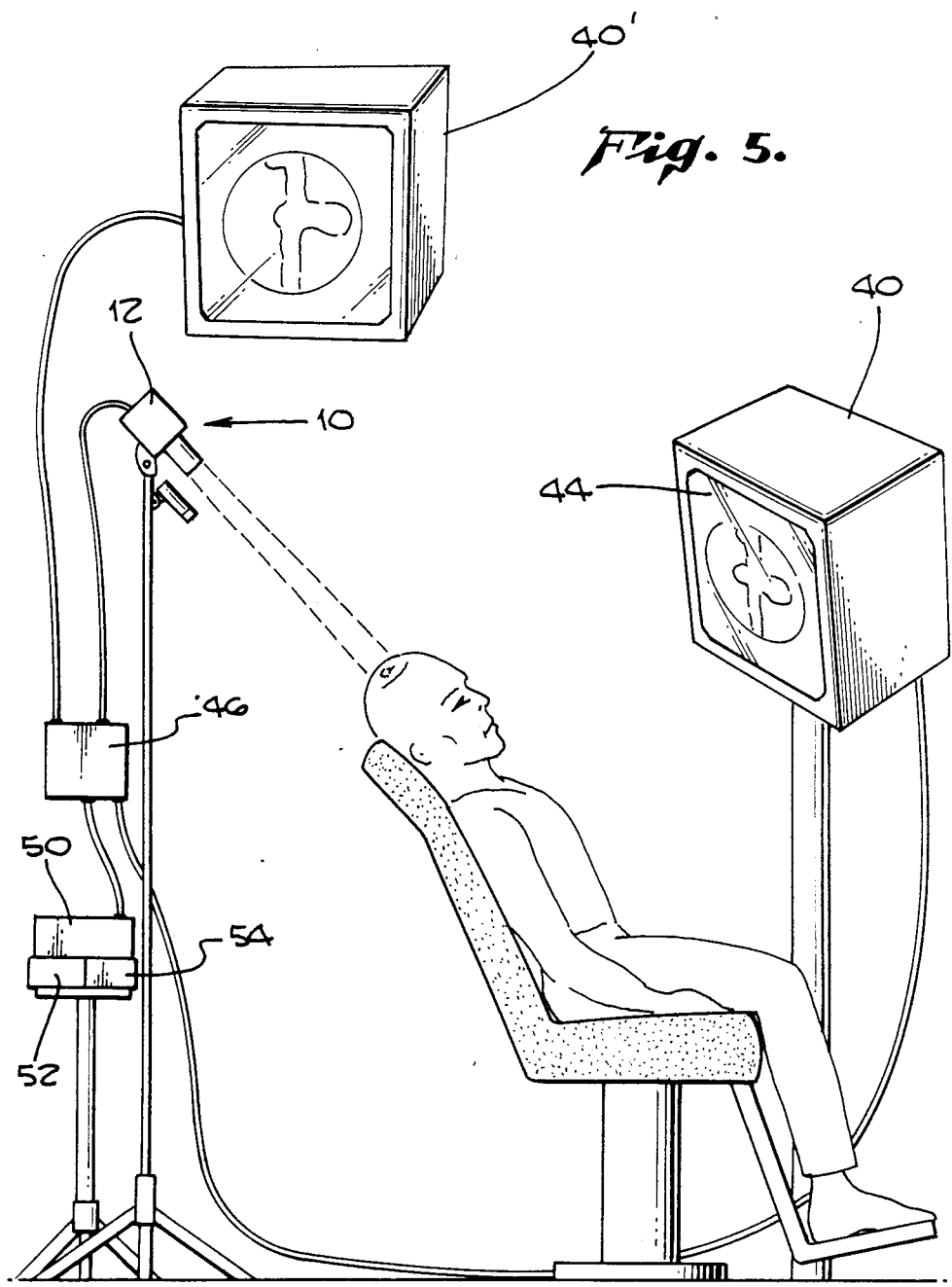
FIG. 5 is a perspective view of an electronic microscope according to the present invention installed in an operating theater together with monitors and auxiliary recording apparatus.

Finally, turning to FIG. 5, there is shown an operating room employing the electronic video system 10 of the present invention. The camera 12 is positioned sufficiently far above the field of interest to permit the introduction of instruments which can be seen, enlarged on the video monitors. The surgeon and assistants can occupy positions around the field of interest so that participation is possible with the aid of the video screens.

Because the optical system provides sufficient depth of field, the lens need not be constantly refocussed to keep all objects of interest in clear focus during a procedure. Moreover, it is possible to use the present electronic video system 10 in combination with endoscopes so long as the camera 12 and the illumination sources have a "line of sight" to the area of interest.

As shown in the Figure, the monitor 40 is positioned to be easily viewed by the principal user of the of the video system 10. Assistants and others may position themselves to view the scene through the same monitor 40 or additional, duplicate monitors 40', may be positioned around the area. For additional viewers who may wish to observe any given procedure, for example, one such monitors 40', is shown.

The brightness of the picture on any monitor is not compromised by the number of monitors since amplification of the video signal can be accomplished either at the camera 12, an intermediate amplifier 46 or at the monitor 40 itself. Accordingly, as many monitors as are deemed appropriate can be provided.

A video recorder 50 can be provided for documentation. The recorder can be connected to the camera 12 or to the intermediate amplifier 46. A color storage memory disc 52, which can store up to twenty five TV type frames, can drive either a high resolution printer (not shown) or some other data recording device. A hard copy printer 54 can be coupled to the system to create a color print of any desired video frame. It is also possible to use either instant photographic cameras or conventional cameras to take a "picture" of the image 42 that is displayed on the video screen 44.

The recording devices can provide a record of any procedure and prints can be made of individual "frames" of the record. Adding additional monitors or recorders does not adversely affect the video display being used by the surgeon or his assistants inasmuch as each additional element of equipment can have the signal that is applied to it amplified electronically.

Thus there has been shown a new and improved electronic device to replace the standard optical surgical microscopes that are currently in use. The electronic device can be from one tenth to one twentieth of the size and weight of the conventional surgical microscope. The magnification can be varied the the use of the zoom lens and the larger monitors. The fatigue associated with long periods of viewing through a binocular eyepiece can be avoided through the use of eye level video monitors. With increased depth of field, both the visual image and the recorded image are clearer and focus need not be constantly adjusted.

This system, the method and variations upon them will occur to those skilled in the art and therefore the scope of the invention should be limited only by the scope of the claims appended hereto.

What is claimed as new is:

1. An apparatus for visualizing a surgical field to assist in microsurgical procedures comprising in combination:
   a. a light source for illuminating the surgical field;
   b. a high resolution video camera having a sensitive image receiving area of from 6–10 mm in diameter;
   c. a large screen, high resolution video monitor coupled to said camera for displaying a greatly enlarged view of the images of the surgical field impinging upon said image receiving area; and
   d. a lens system coupled to said video camera for applying images of the surgical field of said image receiving area, said lens system having a field of view imaging area ranging from 15 to 25 mm in diameter from a distance ranging from 150–500 mm, with a depth of field ranging from 10–20 mm; whereby objects of interest in the surgical field can be displayed on said video motor with a magnification greater than three times to aid in microsurgical procedures so that the video monitor provides the primary image for the performance of such microsurgical procedures.

2. The apparatus of claim 1, above, wherein said lens system of field of 15 mm.

3. The apparatus of claim 1, above, wherein said lens system applies an image to said sensitive image receiving area of from 6–8 mm. in diameter.

4. The apparatus of claim 1, above, wherein said lens system field of view imaging area is 20 mm. in diameter, for viewing objects having a maximum dimension of 20 mm.

5. The apparatus of claim 1, above, wherein said lens system views objects from a distance of from 200 mm. to 400 mm.

6. The apparatus of claim 1, above, wherein the screen of said video monitor is at least 17 inches in diagonal measurement.

7. The apparatus of claim 1, above, wherein the screen of said video monitor is greater than 17 inches in diagonal measurement.

8. The apparatus of claim 1, above, further including recording means coupled to said camera for storing images of objects viewed on said video monitor.

9. The apparatus of claim 1, above, further including record generating means coupled to said camera for producing printed images corresponding to the images displayed on said video monitor.

10. The apparatus of claim 1, above, wherein said lens system includes means for varying the magnification of images without affecting the depth of field.

11. The apparatus of claim 1, above, further including a second video monitor coupled to said camera to permit viewing of images by others than a principal observer.

12. A method of visualizing a surgical field to assist in microsurgical procedures comprising the steps of:
   a. providing a light source of illuminating the surgical field;
   b. providing a high resolution video camera with a sensitive image receiving area of from 6–10 mm in diameter;
   c. coupling a large screen, high resolution video monitor to said camera for displaying a greatly enlarge view of the images impinging upon said image receiving area; and
   d. coupling a lens system to said video camera for applying images of the surgical field to said image receiving area thereof, said lens system being capable of viewing an image ranging from 15 to 25 mm in diameter from a distance ranging from 150–500 mm, with a depth of field ranging from 10–20 mm; whereby objects of interest in the surgical field can be displayed on said video monitor with a magnification greater than three times so that that a video monitor provides the primary images for performing such microsurgical procedures.

13. The method of claim 12, above, wherein said lens system has a depth of field of 15 mm.

14. The method of claim 12, above, wherein said lens system applies an image to said sensitive image receiving area of from 6–8 mm. in diameter.

15. The method of claim 12, above, wherein said lens system can view objects up to a maximum dimension of 20 mm.

16. The method of claim 12, above, wherein said lens system views objects from a distance of from 200 mm. to 400 mm.

17. The method of claim 12, above, wherein the screen of said video monitor upon which images are displayed is at least 17 inches in diagonal measurement.

18. The method of claim 12, above, wherein the screen of said video monitor is greater than 17 inches in diagonal measurement.

19. The method of claim 12, above, further including the step of recording images of objects viewed on said video monitor 20. The method of claim 12, above, further including the step of producing printed images corresponding to the images displayed on said video monitor.

21. The method of claim 12, above, including the step of varying the magnification of images by said lens system without affecting the depth of field.

22. The method of claim 12, above, further including the step of coupling a second video monitor to said camera to permit viewing of images by others than a principal observer.

* * * * *